(12) United States Patent
Byron

(10) Patent No.: US 9,326,955 B2
(45) Date of Patent: May 3, 2016

(54) COMBINATION PHARMACEUTICALS AND METHODS THEREOF USING PROTEINACIOUS CHANNELS AS TREATMENTS FOR MEDICAL CONDITIONS

(71) Applicant: Loyola University Chicago, Maywood, IL (US)

(72) Inventor: Kenneth L. Byron, Chicago, IL (US)

(73) Assignee: Loyola University Chicago, Maywood, IL (US)

( * ) Notice: Subject to any disclaimer, the term of this patent is extended or adjusted under 35 U.S.C. 154(b) by 59 days.

(21) Appl. No.: 14/174,902

(22) Filed: Feb. 7, 2014

(65) Prior Publication Data

US 2014/0155368 A1 Jun. 5, 2014

Related U.S. Application Data

(63) Continuation-in-part of application No. 12/814,640, filed on Jun. 14, 2010, now Pat. No. 8,686,017, and a continuation-in-part of application No. 12/609,724, filed on Oct. 30, 2009, now Pat. No. 8,785,466.

(60) Provisional application No. 61/110,152, filed on Oct. 31, 2008.

(51) Int. Cl.
| | |
|---|---|
| *A61K 31/38* | (2006.01) |
| *A61K 31/155* | (2006.01) |
| *A61K 31/167* | (2006.01) |
| *A61K 31/27* | (2006.01) |
| *A61K 31/415* | (2006.01) |
| *A61K 31/555* | (2006.01) |
| *G01N 33/50* | (2006.01) |
| *G01N 33/68* | (2006.01) |

(52) U.S. Cl.
CPC ............... *A61K 31/167* (2013.01); *A61K 31/27* (2013.01); *A61K 31/415* (2013.01); *A61K 31/555* (2013.01); *G01N 33/5038* (2013.01); *G01N 33/6872* (2013.01); *G01N 2800/122* (2013.01); *G01N 2800/32* (2013.01)

(58) Field of Classification Search
USPC .................................................. 514/635, 432
See application file for complete search history.

(56) References Cited

U.S. PATENT DOCUMENTS 6,579,892 B1 * 6/2003 Starck .................. C07D 249/12
514/365

FOREIGN PATENT DOCUMENTS

EP 1407768 * 4/2014

OTHER PUBLICATIONS

Prenner, Current Opinion in Pulmonary Medicine, 2008;14:57-63.*

* cited by examiner

*Primary Examiner* — San-Ming Hui
(74) *Attorney, Agent, or Firm* — Hartman Global IP Law; Gary M. Hartman; Domenica N. S. Hartman

(57) ABSTRACT

Methods and combination pharmaceuticals for treating bronchospastic medical conditions by utilizing the electrophysiology of proteinacious channels in lipid membranes of mammalian cells. The combination pharmaceuticals include at least one β-adrenergic receptor agonist, and at least one composition adapted to effect the electrophysiology of Kv7 potassium channels of a lipid membrane of an airway smooth muscle cell. The pharmaceutical may be administered to a living body in a therapeutic amount sufficient to activate the Kv7 potassium channels of an airway smooth muscle cell.

15 Claims, 13 Drawing Sheets

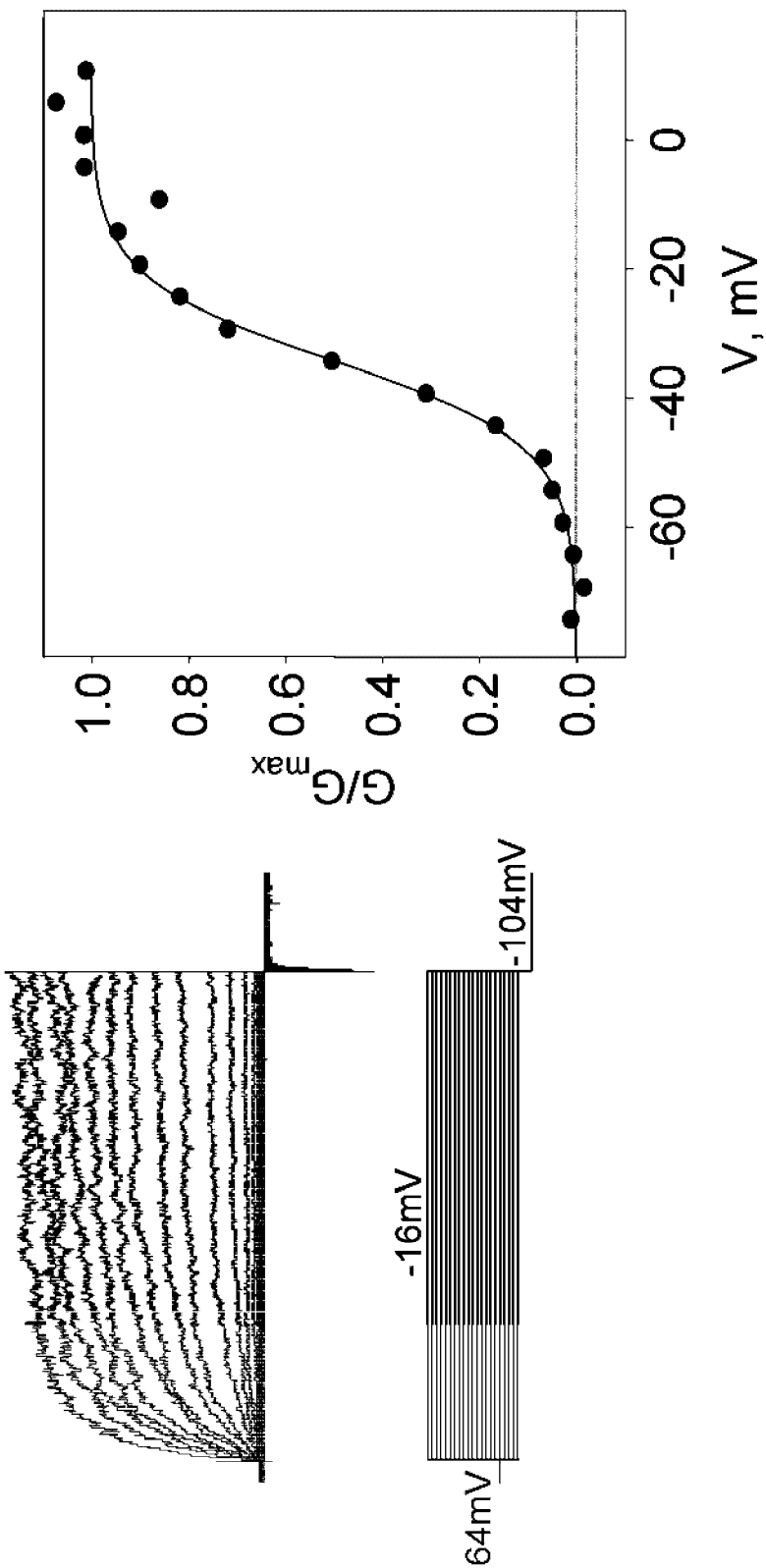

COMBINATION PHARMACEUTICALS AND METHODS THEREOF USING PROTEINACIOUS CHANNELS AS TREATMENTS FOR MEDICAL CONDITIONS

CROSS REFERENCE TO RELATED APPLICATIONS

This is a continuation-in-part patent application of co-pending U.S. patent application Ser. No. 12/814,640, filed Jun. 14, 2010, which was a continuation-in-part patent application of prior co-pending U.S. patent application Ser. No. 12/609,724, filed Oct. 30, 2009, which claimed benefit of U.S. provisional patent application Ser. No. 61/110,152, filed Oct. 31, 2008. The contents of these prior applications are incorporated herein by reference.

BACKGROUND OF THE INVENTION

The present invention generally relates to therapeutic strategies utilizing proteinacious channels in lipid membranes of mammalian cells. More particularly, this invention relates to the utilization of the electrophysiology of Kv7 potassium channels and/or L-type calcium channels in vascular smooth muscle cells (VSMCs) and airway smooth muscle cells (ASMCs), and to the use thereof to identify new pharmaceuticals that may be used to treat cardiovascular and airway conditions, including hypertension, stroke and asthma, and to perform drug screening to assess potential risk of pharmaceuticals.

Mammalian cells, including the smooth muscle cells (SMCs) within the walls of arteries (vascular smooth muscle cells, or VSMCs) and the bronchioles of the lung (airway smooth muscle cells, or ASMCs), are surrounded by a lipid membrane which functions as a barrier to diffusion of many soluble substances, including ions, into and out of the cytosol of the cells. Proteinacious channels integrated into these lipid membranes allow ions to cross the lipid membrane when the channels are open. A portion of these proteinacious channels is selective for potassium ions ($K^+$), and are referred to as potassium channels or $K^+$ channels. Still other proteinacious channels are selective for calcium ions ($Ca^{2+}$), and are referred to as calcium channels or $Ca^{2+}$ channels. Under normal circumstances, potassium ions ($K^+$) are typically present inside the cell at concentrations about twenty-five times higher as compared to their corresponding concentration outside the cell. When these potassium channels open (activate), potassium ions ($K^+$) tend to leak out of the cell through these potassium channels, resulting in a measurable electrical current across the membrane. This electrical current establishes an electrical charge difference across the lipid membrane (membrane voltage, or $V_m$), resulting in the polarization of the membrane. Polarization of the membranes of smooth muscle cells has a profound effect on the function of voltage-sensitive L-type $Ca^{2+}$ channels in these cells.

VSMCs and ASMCs are able to contract or relax to regulate blood flow (and blood pressure) and airway resistance, respectively. The contractile state of SMCs is determined by the cytosolic $Ca^{2+}$ concentration ($[Ca^{2+}]_{cyt}$). Elevation of $[Ca^{2+}]_{cyt}$ triggers SMC contraction to produce vasoconstriction or airway constriction. Influx of $Ca^{2+}$ through L-type $Ca^{2+}$ channels is a major mechanism for elevation of cytosolic $[Ca^{2+}]$ in SMCs and this depends on membrane voltage ($V_m$). As noted above, $K^+$ channels represent a primary effector for adjusting $V_m$. $K^+$ channels of the Kv7 family (also known as KCNQ) were recently identified among the cohort of vascular ion channels. These Kv7 channels, which were previously recognized as mediators of acetylcholine-induced neuronal excitation, have distinctive electrophysiological characteristics: activation at voltages negative to −50 mV, outward rectification, and absence of time-dependent inactivation.

Because polarization of the membranes of SMCs has a profound effect on the function of voltage-sensitive L-type $Ca^{2+}$ channels in these cells, cell membrane polarization is also a primary determinant of the extent to which arteries and bronchioles constrict or dilate. KCNQ voltage-activated $K^+$ channels play an important role in regulating the membrane voltage of many excitable tissues. See, for example, Delmas et al., "Pathways modulating neural KCNQ/M (Kv7) potassium channels," Nat Rev Neurosci 6(11):850-862 (2005); and Robbins et al., KCNQ potassium channels: physiology, pathophysiology, and pharmacology," Pharmacol Ther 90(1): 1-19 (2001). Recently, KCNQ5 (Kv7.5) channels were determined to be expressed and functional in vascular smooth muscle cells.

Cyclooxygenase-2 (COX-2) inhibitors are important members of the family of non-steroidal anti-inflammatory drugs (NSAIDs). Celebrex® (celecoxib) and Vioxx® (rofecoxib) were introduced in 1999 and rapidly became frequently prescribed for clinical use as analgesic/anti-inflammatory agents because they prevent the generation of prostaglandins involved in inflammation and pain, while sparing the beneficial effects of cyclooxygenase-1 (COX-1)-generated prostanoids. However, COX-2 inhibitors have been under intense scrutiny since 2004 when Vioxx® was voluntarily withdrawn from the market because of a reported increased risk of myocardial infarction and stroke in patients taking the drug for prolonged periods of time.

A systematic review of randomized clinical trials of COX inhibitors revealed that rofecoxib, a highly COX-2-selective agent, and diclofenac, an NSAID with COX-2/COX-1 selectivity similar to celecoxib, both significantly increased the risk of cardiovascular (CV) events. In contrast, a number of clinical studies failed to demonstrate an increased CV risk with celecoxib relative to placebo. See, for example, McGettigan et al., "Cardiovascular Risk and Inhibition of Cyclooxygenase: A Systematic Review of the Observational Studies of Selective and Nonselective Inhibitors of Cyclooxygenase 2," Journal of the American Medical Association 296:1633-1644 (2006), and White et al., "Risk of Cardiovascular Events in Patients Receiving Celecoxib: A Meta-Analysis of Randomized Clinical Trials," The American Journal of Cardiology 99(1):91-98 (2007). The reasons for the differences between celecoxib and other COX-2 inhibitors have been widely debated.

HERG (human ether-a-go-go related gene) encodes a particular type of potassium channel (Kv11.1) that contributes to the electrical activity of the heart. To avoid unwanted cardiac side effects, new drugs in development are commonly screened for effects on Kv11.1 potassium channel currents using cultured cells engineered to express large numbers of these channels. In contrast, smooth muscle Kv7 channels have not been recognized as a potential site of adverse (or beneficial) drug action and therefore no airway or vascular smooth muscle Kv7 channel screening assays have been developed. Prior to a recent report (Brueggemann et al., "Differential Effects of Selective COX-2 Inhibitors on Vascular Smooth Muscle Ion Channels May Account for Differences in Cardiovascular Risk Profiles," Molecular Pharmacology 76: 1053-1061 (2009)), COX inhibitors had not been reported to exert any effects on vascular smooth muscle Kv7 channels or vascular smooth muscle L-type $Ca^{2+}$ channels, and therefore no therapeutic strategies have been proposed to use these drugs to treat vasospasm or bronchospasm that can lead to heart attacks and strokes or airway obstruction, respectively.

HERG channel screening assays do not detect effects of drugs on smooth muscle Kv7 channel activity and therefore are not useful for predicting potential adverse cardiovascular side effects associated with such activity or for predicting potential beneficial therapeutic effects associated with such activity.

BRIEF DESCRIPTION OF THE INVENTION

The present invention provides methods of treating bronchospastic medical conditions and pharmaceuticals therefor that utilize the electrophysiology of proteinacious channels in lipid membranes of mammalian cells.

According to one aspect of the invention, a combination pharmaceutical includes at least one β-adrenergic receptor agonist, and at least one composition adapted to effect the electrophysiology of Kv7 potassium channels of a lipid membrane of an airway smooth muscle cell.

According to another aspect of the invention, a method of treating a bronchospastic condition that can lead to airway obstruction in a living body includes administering a pharmaceutical to the living body in a therapeutic amount sufficient to activate the Kv7 potassium channels of an airway smooth muscle cell.

According to yet another aspect of the invention, the method can further include administering at least a second pharmaceutical comprising a β-adrenergic receptor agonist to the living body.

A technical effect of the invention is the ability to treat bronchospastic medical conditions, such as asthma, by effecting the electrophysiology of Kv7 potassium channels of a lipid membrane of an airway smooth muscle cell. It is particularly believed that combination therapies may provide benefits of both the Kv7 potassium channel effecting composition and the β-adrenergic receptor agonist while also reducing the desensitization of the β-adrenergic receptor agonist.

Other aspects and advantages of this invention will be better appreciated from the following detailed description.

BRIEF DESCRIPTION OF THE DRAWINGS

FIGS. 4 through 7 are four plots of Kv7 currents in freshly isolated ASMCs. FIG. 4 is representative of raw currents recorded from a series of 5s voltage steps. FIG. 5 is a normalized conductance plot determined from tail currents and fit with a Boltzmann function ($V_{0.5}$=−34 mV). FIG. 6 is current-voltage (I-V) plot that illustrates reversible enhancement of currents by Kv7 channel activator flupirtine and near complete suppression of currents by the Kv7 channel blocker linopirdine. FIG. 7 is representative of a time course of current enhancement by 10 µM celecoxib measured at a holding potential of −20 mV.

FIGS. 10A, C, and E show representative time courses of retigabine- (FIG. 10A; 10 µM, cell capacitance (C)=23.6 pF), ZnPyr- (FIG. 10C; 100 nM, C=14.3 pF), and DMC- (FIG. 10E; 10 µM, C=20.2 pF) induced enhancement of endogenous KCNQ currents recorded in ASMCs at −20 mV holding voltage. A break in the recording (10 minutes) is indicated by 2 vertical gray lines. FIGS. 10B, D, F represent I-V relationships of KCNQ currents recorded in ASMCs before (control, filled circles), during treatment with 10 µM retigabine (FIG. 10B; open circles, n=3), during treatment with 100 nM ZnPyr (FIG. 10D; open circles, n=4), or during treatment with 10 µM DMC (FIG. 10F; open circles, n=7), and after 5 minute treatment with the KCNQ channel blocker XE991 in the presence of each activator (10 µM, filled triangles). An asterisk * indicates a significant difference from control (One Way Repeated Measures ANOVA, p<0.05).

DETAILED DESCRIPTION OF THE INVENTION

As discussed in greater detail below, the present invention arises in part from the determination that Kv7 currents in myocytes from rat arteries are suppressed by vasoconstrictor hormones and are sensitive to selective Kv7 channel inhibitors, such as linopirdine and XE-991, and Kv7 channel activators, such as flupirtine and retigabine. Moreover, based on molecular approaches (RNA interference and expression of dominant-negative subunits) performed in investigations (discussed below) leading to the present invention, there is extensive evidence that functional Kv7 channels in mesenteric artery myocytes include Kv7.5 as an essential subunit.

Figure 2:
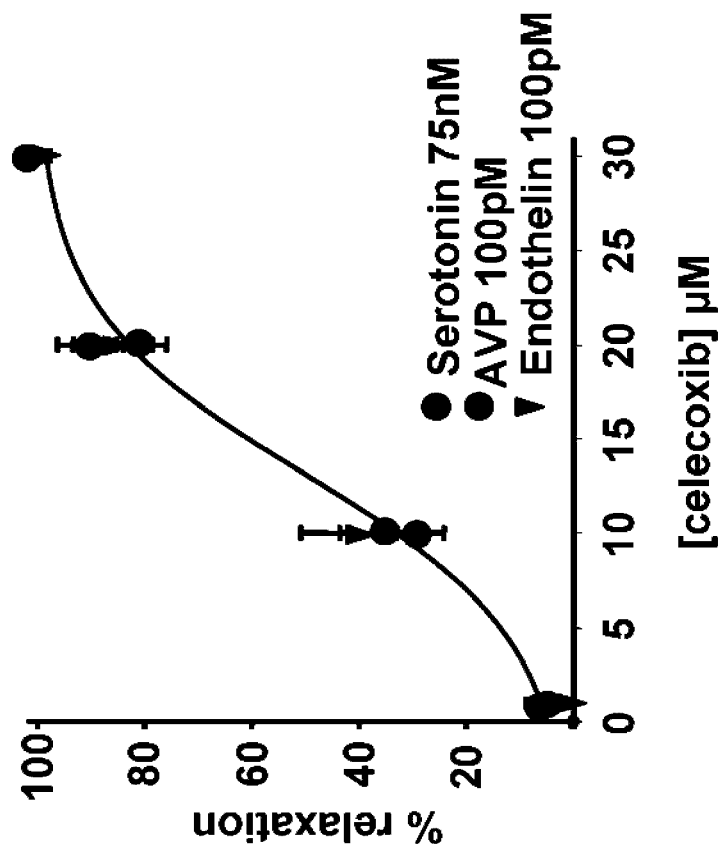
FIG. 2 is a plot of mean concentration-response data expressed as percent of maximal dilation for basilar arteries pre-constricted with serotonin, vasopressin (AVP), or endothelin.
Figure 1:
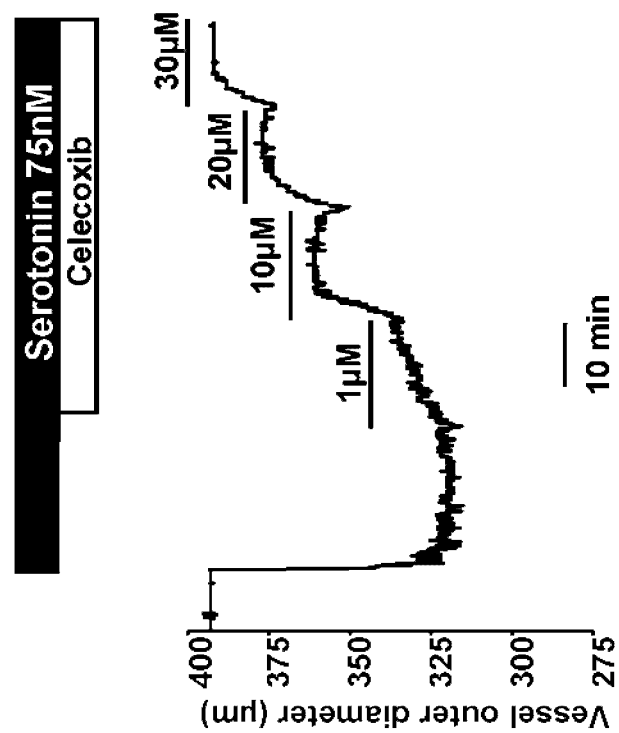
FIG. 1 is a plot representing concentration-dependent vasodilation in response to the Kv7 channel activator celecoxib following pre-constriction of a rat basilar artery with 75 nM serotonin.
Figure 3:
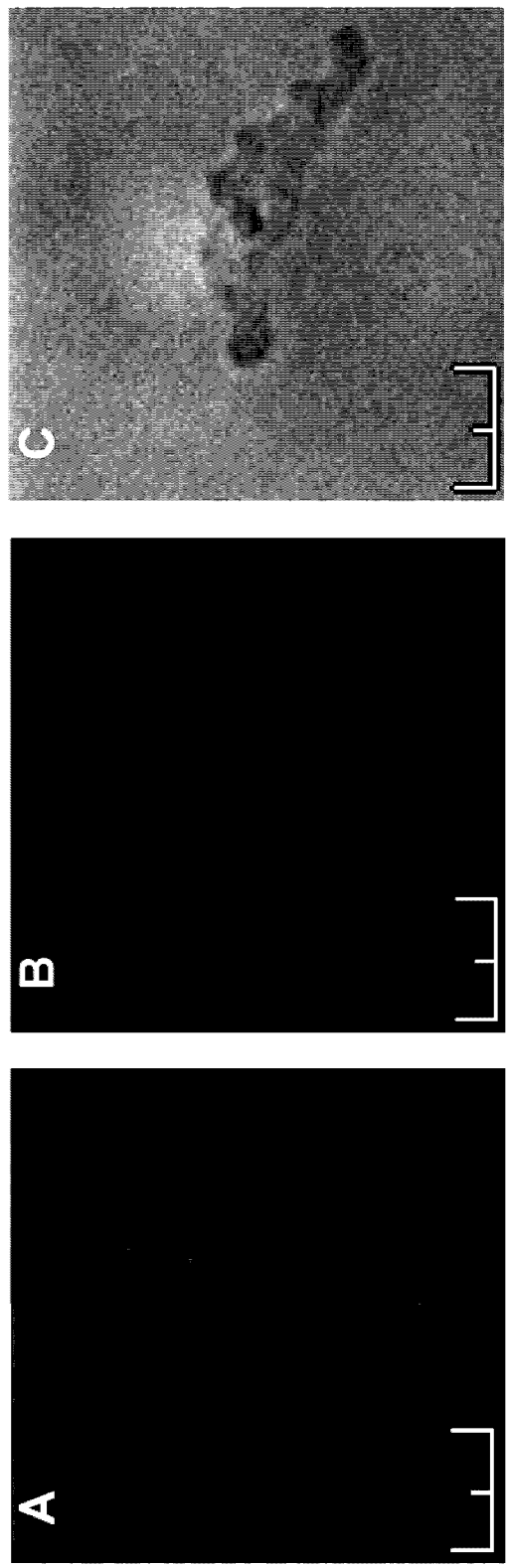
FIG. 3 shows three scanned images evidencing the detection of KCNQ5 (Kv7.5) channels by immunostaining of guinea pig ASMC. Image A is of guinea pig ASMC immunostained with anti-Kv7.5. Image B is a minus primary antibody control image captured at the same gain and exposure as image A. Image C shows the same cell as image B, but captured under phase contrast illumination. The horizontal bars in each image represents twenty micrometers.

These investigations also confirmed the function of Kv7 channels in isolated pressurized mesenteric arteries and demonstrated their role in determining mesenteric vascular resistance (MVR) and mean arterial pressure (MAP) measured in anesthetized instrumented Sprague-Dawley rats. Flupirtine produced significant dose-dependent decreases in MAP and MVR, whereas linopirdine had the opposite effects. Other clinically used drugs, including the cyclooxygenase-2 (COX-2) inhibitors celecoxib and diclofenac, also have pronounced effects on vascular Kv7 channels. Celecoxib also acts as a calcium channel blocker in vascular myocytes, making it a very effective vasodilator and anti-vasospastic agent. As evidence, FIG. 1 is a plot representing concentration-dependent vasodilation in response to the Kv7 channel activator celecoxib following pre-constriction of a rat basilar artery with 75 nM serotonin, and FIG. 2 is a plot of mean concentration-response data expressed as percent of maximal dilation for basilar arteries pre-constricted with serotonin, vasopressin (AVP), or endothelin.

As also discussed in greater detail below, the investigations leading to the present invention also determined that Kv7 channels are expressed in guinea pig airway SMCs, where they can be modulated by pharmacological agents to enhance or suppress their function.

In view of the above, the present invention proposes that smooth muscle Kv7 channels may represent an important new therapeutic target for treatment of cardiovascular and airway conditions, including but not limited to such diseases as asthma, hypertension and stroke.

A first aspect of the present invention arises from investigations that suggest that differential effects of Vioxx® (rofecoxib), Celebrex® (celecoxib), and other COX-2 inhibitors on vascular Kv7 channels and L-type $Ca^{2+}$ channels may account for the differences in cardiovascular risk profiles of these drugs. In particular, investigations leading to certain aspects of the present invention have identified celecoxib as an effective activator of vascular Kv7 channels and an effective inhibitor of vascular L-type $Ca^{2+}$ channels, whereas rofecoxib does not exhibit either effect. These investigations are reported in Brueggemann et al., "Differential Effects of Selective COX-2 Inhibitors on Vascular Smooth Muscle Ion Channels May Account for Differences in Cardiovascular Risk Profiles," Molecular Pharmacology 76: 1053-1061 (2009), whose entire contents are incorporated herein by reference. According to particular aspects of the invention, such differential effects provide a basis for using vascular Kv7 potassium channel electrophysiology, for example, to identify new pharmaceuticals that may be capable of treating vasospastic conditions, and to perform drug screening to assess potential cardiovascular risk of pharmaceuticals.

In studies leading to the present invention and reported in Mackie et al., "Cardiovascular KCNQ (Kv7) Potassium Channels: Physiological Regulators and New Targets for Therapeutic Intervention," Mol Pharmacol 74:1171-1179 (2008) (incorporated herein by reference), Kv7 channel modulators used clinically to treat a number of neuronal disorders were determined to have pronounced effects on vascular Kv7 channels. The studies further showed that these effects were associated with corresponding changes in vascular tone in isolated pressurized rat mesenteric arteries and changes in systemic blood pressure and mesenteric vascular resistance in live rats. In subsequent studies reported in Brueggemann et al. (supra), by screening drugs with structures similar to Kv7 channel modulators but used for other clinical applications, an aspect of the present invention is the identification of the COX-2 inhibitor celecoxib (as disclosed in, for example, U.S. Pat. Nos. 5,466,823, 5,563,165, 5,760,068 and 5,972,986, whose contents regarding the chemical structure of celecoxib are incorporated herein by reference) as a potent and effective activator of vascular Kv7 channels. This conclusion is believed to have important and broader implications relating to the treatment of vasospastic conditions with pharmaceuticals, and screening to assess potential cardiovascular risk of pharmaceuticals.

Preliminary findings leading to this invention were derived from electrophysiological analyses of the effects of celecoxib and rofecoxib on rat and human vascular smooth muscle cell (VSMC) ion channels. The activities were measured for two types of ion channels that are perhaps the most important in determining the contractile state of vascular smooth muscle cells: potassium ($K^+$) channels, which determine the resting membrane voltage, and voltage-sensitive calcium ($Ca^{2+}$) channels (VSCC), the activation of which allows $Ca^{2+}$ influx and vasoconstriction. These investigations showed that both types of ion channels are affected by celecoxib, and that celecoxib is a potent activator of Kv7.5 potassium channels and an inhibitor of L-type $Ca^{2+}$ channels in vascular smooth muscle cells. These effects, which were apparent at concentrations of celecoxib often achieved with clinical therapy, had never been reported previously and may account for the reduced risk of cardiovascular side effects with celecoxib treatment as compared to rofecoxib. Rofecoxib did not mimic celecoxib in its effects on either Kv7.5 channels or L-type VSCC. The actions of these drugs can be assessed at the level of isolated arterial myocytes and intact pressurized arteries. Also demonstrated was the ability to monitor effects of Kv7 channel activators on systemic blood pressure and mesenteric vascular resistance in live rats. These functional assays provide a means for screening new drugs as well as drugs already in clinical use, and a means for predicting potential CV side effects.

The significance of the above extends beyond the well known and abundant use of COX-2 inhibitors as anti-inflammatory agents. In recent years there has been an explosion of interest in the use of COX-2 inhibitors as anti-cancer drugs. In cancers and abnormal growths in the intestinal tract, COX inhibitors have been shown to reduce the occurrence of cancers and pre-cancerous growths. As reported by Zhu et al. in "Using Cyclooxygenase-2 Inhibitors as Molecular Platforms to Develop a New Class of Apoptosis-Inducing Agents," J Natl Cancer Inst 94(23):1745-1757 (2002), whose contents are incorporated herein by reference, several dozen analogs of celecoxib have been generated with small alterations in their chemical structures. As used herein, an analog of celecoxib is defined as a structural variant of celecoxib with different chemical substitutions around the diarylpyrazole moiety which forms the core structure of celecoxib, for example, as described by Penning et al. (Journal of Medicinal Chemistry 40 (9): 1347-1365, 1997) and as utilized by Schonthal et al. (Expert Opin Investig Drugs 17, 197-208, 2008) to evaluate anti-cancer efficacy of celecoxib and its analogs). Some of these analogs retained COX-2 inhibitory activity, whereas many others did not. As reported by Zhu et al. as well as Schonthal et al. in "Celecoxib analogs that lack COX-2 inhibitory function: preclinical development of novel anticancer drugs," Expert Opinion on Investigational Drugs 17(2):197-208 (2008), the anti-tumor potency of celecoxib analogs do not correlate with COX-2 inhibitory activity, suggesting that inhibition of COX-2 is not essential for the anti-cancer effects. One of these compounds, 2,5-dimethyl-celecoxib, which has no detectable COX-2 inhibitory activity, has been reported to display stronger anti-cancer activity than celecoxib itself. Schönthal "Antitumor properties of dimethyl-celecoxib, a derivative of celecoxib that does not inhibit cyclooxygenase-2: implications for glioma therapy," Neurosurg Focus 20(4):E21 (2006). In studies leading to the present invention, 2,5-dimethyl-celecoxib was determined to be a potent activator of vascular Kv7 channels and an inhibitor of vascular L-type calcium channels. The mechanisms underlying the anti-cancer efficacy of celecoxib and its analogs are the subject of much controversy. The anti-cancer efficacy of celecoxib analogs may relate to their previously unrecognized effects on vascular smooth muscle Kv7 channels or other vascular ion channels. Characterization of these effects may also help to predict potential cardiovascular side effects of celecoxib or its analogs when used as anti-cancer agents or to develop new clinical applications for celecoxib or its analogs (for example, 2,5-dimethyl-celecoxib) as, for example, an antivasospastic and/or antihypertensive agent.

An additional preferred aspect of the invention is to develop new therapeutic applications for Kv7 channel modulators based on the roles of these channels in vascular smooth muscle physiology. In studies leading to the present invention, the signal transduction process by which vasoactive hormones induce constriction of arteries was determined to involve inhibition of Kv7.5 K$^+$ channels. Mackie et al. (above) and Brueggemann et al., "Vasopressin stimulates action potential firing by protein kinase C-dependent inhibition of KCNQ5 in A7r5 rat aortic smooth muscle cells," Am J Physiol Heart Circ Physiol 292(3):H1352-H1363 (2007), disclose what is believed to be the first evidence that these channels are regulated by the vasoconstrictor hormone, arginine-vasopressin (AVP), acting on vascular smooth muscle cells, and that this effect is central to its physiological vasoconstrictor actions. The vasoconstrictor actions of AVP are important in terms of normal physiological blood pressure regulation, and AVP has also been implicated in a number of cardiovascular diseases, including spasm of the cerebral vasculature that occurs in a condition called subarachnoid hemorrhage (SAH). Cerebral vasospasm represents a significant clinical problem and is a major form of stroke in the United States. The mechanisms underlying vasospasm after SAH are an area of active investigation in which no consensus has been reached. Furthermore, clinical therapies to prevent vasospasm or reduce its detrimental effects are currently inadequate. A notable aspect of the present invention is to propose that Kv7 channel activators, including celecoxib, may be used as a novel therapy to protect against SAH-induced stroke.

The scope of the present invention further encompasses the tools used to measure vascular Kv7 channel activities and/or functional contributions of these channels in vascular smooth muscle cells. To screen new or existing drugs for potential vascular side effects associated with changes in vascular smooth muscle Kv7 channel activity, varying concentrations of the drugs should be applied to cells expressing these channels while recording the electrical activity that results from changes in channel opening. Patch clamp electrophysiological techniques are typically used for such recordings, and investigations leading to the present invention have developed patch clamp recording techniques for accurate and sensitive monitoring of Kv7 channel activity in vascular smooth muscle cells. Drugs that significantly increase vascular smooth muscle Kv7 channel activity at concentrations achieved clinically (for example, flupirtine and retigabine) are expected to have reduced risk of cardiovascular side effects, whereas drugs that reduce vascular smooth muscle Kv7 channel activity may have increased risk of cardiovascular side effects. For example, flupirtine is a known Kv7 channel activator used to treat pain; plasma concentrations achieved clinically can be as high as about 12 µM with a 100 mg dose (Abrams et al., "Pharmacokinetics of flupirtine in elderly volunteers and in patients with moderate renal impairment," Postgraduate Medical Journal, 64: 361-363 (1988)) and doses up to about 600 mg are routinely given to treat chronic pain. In patients with rheumatic disease, flupirtine (about 100 to 600 mg per day) was reported to lower systolic blood pressure (Herrmann et al., "On the adverse reactions and efficacy of long-term treatment with flupirtine: preliminary results of an ongoing twelve-month study with 200 patients suffering from chronic pain states in arthrosis or arthritis," Postgraduate Medical Journal, 63: 87-103 (1987)). This might have been predicted based on observations made during investigations leading to the present invention that a concentration of 10 µM flupirtine was sufficient to increase vascular Kv7 current by 100%. Further indications to support such predictions may be obtained by measuring the effects of drugs on constriction/dilation of pressurized arteries. Flupirtine (about 10 to 40 µM) was found to dilate rat mesenteric arteries (Mackie et al., "Vascular KCNQ potassium channels as novel targets for the control of mesenteric artery constriction by vasopressin, based on studies in single cells, pressurized arteries, and in vivo measurements of mesenteric vascular resistance," Journal of Pharmacology and Experimental Therapeutics 325: 475-483 (2008)).

According to an aspect of the invention, screening of drugs for effects on vascular Kv7 channel activity may identify new drugs or new applications for existing drugs for the treatment of cardiovascular diseases. For example, by screening COX inhibitors for effects on vascular Kv7 channels, the present invention identified celecoxib as a potent vascular Kv7 channel activator and determined that celecoxib is a potent vasodilator that can reverse AVP-induced basilar artery constriction. On this basis, one aspect of the present invention proposes a treatment in which celecoxib is used effectively to reduce stroke associated with spasm of basilar and/or cerebral arteries.

Prior to investigations leading to the invention, drugs in clinical use had not been screened for effects on vascular Kv7 channels. Such screening might have predicted the differential effects of celecoxib and rofecoxib in terms of their potential risks of adverse cardiovascular events. Furthermore, had such screening methods been employed previously, celecoxib might have been previously identified as a potentially useful anti-vasospastic agent. Therefore, by employing screening techniques to evaluate the effects of new or existing drugs on vascular Kv7 channels, adverse side effects may be suppressed or prevented and new therapeutic applications for drugs may be realized.

The present invention is believed to provide a basis for the effect of COX-2 inhibitors on vascular Kv7 channels and for performing drug screening using Kv7 channel electrophysiology to assess potential cardiovascular risk. Furthermore, the determination that celecoxib and its analog 2,5-dimethyl-celecoxib are effective activators of vascular Kv7 channels and effective inhibitors of vascular L-type Ca$^{2+}$ channels is also believed to have been unknown prior to the present invention. As such, the present invention also encompasses methods of treating a hypertensive or vasospastic condition in a living body by administering a pharmaceutical, for example, celecoxib or an analog thereof (as a nonlimiting example, 2,5-dimethyl-celecoxib), as an antivasospastic and/or antihypertensive agent that can be administered in a therapeutic amount sufficient to activate vascular Kv7 potassium channels and/or inhibit vascular L-type calcium channels.

As previously noted, a second aspect of the present invention arises from investigations evidencing that smooth muscle Kv7 channels may represent an important new therapeutic target for treatment of airway conditions, including but not limited to such diseases as asthma and other bronchospastic conditions that can lead to airway obstruction.

In asthma, airway constriction results largely from hypercontraction of airway smooth muscle cells (ASMCs). ASMC hypercontraction may result from elevation of cytosolic calcium ($Ca^{2+}$) concentration due to activation of voltage-sensitive $Ca^{2+}$ channels (VSCC) in ASMCs. The mechanism discussed above regarding the suppression of $K^+$ channel activity in vascular smooth muscle cells prompted speculation that the suppression of $K^+$ channel activity may also function in ASMCs by providing the stimulus for activation of VSCCs. The results of investigations reported below provide evidence that the same $K^+$ channels (KCNQ or Kv7 channels) are present in ASMCs. Although these channels have not previously been identified in these cells, it is hypothesized that they are important in ASMC function, that their activity may be suppressed by inflammatory mediators present in asthmatic lungs to induce airway constriction, and that their activity can be increased by clinically used Kv7 channel activators to induce airway smooth muscle relaxation.

A common feature in the etiology of asthma is the development of airway hyperresponsiveness, defined as the exaggerated narrowing of the airways, a process involving hypercontraction of airway smooth muscle cells (ASMCs). As in other classes of smooth muscle (including VSMCs), contraction of ASMCs is triggered by an elevation of cytosolic calcium concentration ($[Ca^{2+}]_{cyt}$). Although there is little consensus as to the mechanisms primarily responsible for regulating $[Ca^{2+}]_{cyt}$ in ASMCs in healthy or in diseased lungs, there is considerable evidence that voltage-sensitive $Ca^{2+}$ channels (VSCC) play an important role in elevating $[Ca^{2+}]_{cyt}$ to induce ASMC contraction. $K^+$ channels in ASMCs are important because their activity serves as a hyperpolarizing mechanism to maintain negative resting voltages and thereby prevent opening of VSCC. $K^+$ channel activators have been proposed as therapeutic agents to treat airway hyperresponsiveness, but no useful drugs have yet been developed to target the $K^+$ channels previously found to be expressed in ASMCs. There is, however, a well established pharmacopoeia of Kv7 channel activators, which are used clinically for treatment of epilepsy and pain. The investigations reported below provide evidence that Kv7 channels are expressed in ASMCs, including evidence that implicates these Kv7 channels as both mediators of ASMC contraction and targets for therapeutic intervention A first investigation relating to this aspect of the invention was directed to investigating the expression of Kv7 channels in ASMCs. Using quantitative RT-PCR (reverse transcription polymerase chain reaction), expression of multiple KCNQ subtypes were detected in human trachealis muscle, which showed abundant expression of KCNQ1, barely detectable expression of KCNQ2 or KCNQ3, and modest expression of KCNQ4 and KCNQ5 mRNAs (Brueggemann et al., "Kv7 potassium channels in airway smooth muscle cells: signal transduction intermediates and pharmacological targets for bronchodilator therapy," Am J Physiol Lung Cell Mol Physiol, 302, L120-L132 (2012)). The corresponding Kv7 channel proteins were also detected by immunohistochemistry in ASMCs isolated from human trachealis muscle. Predominant expression of KCNQ1, KCNQ4, and KCNQ5 has also recently been reported for rat and mouse tracheal is muscle (Evseev et al., "Functional effects of KCNQ $K^+$ channels in airway smooth muscle," Front Physiol, 4, doi: 10.3389/fphys.2013.00277 (2013); Brueggemann et al., "KCNQ (Kv7) potassium channel activators as bronchodilators: combination with a $\beta_2$-adrenergic agonist enhances relaxation of rat airways," Am J Physiol Lung Cell Mol Physiol (in press)).

Figures 6, 7:
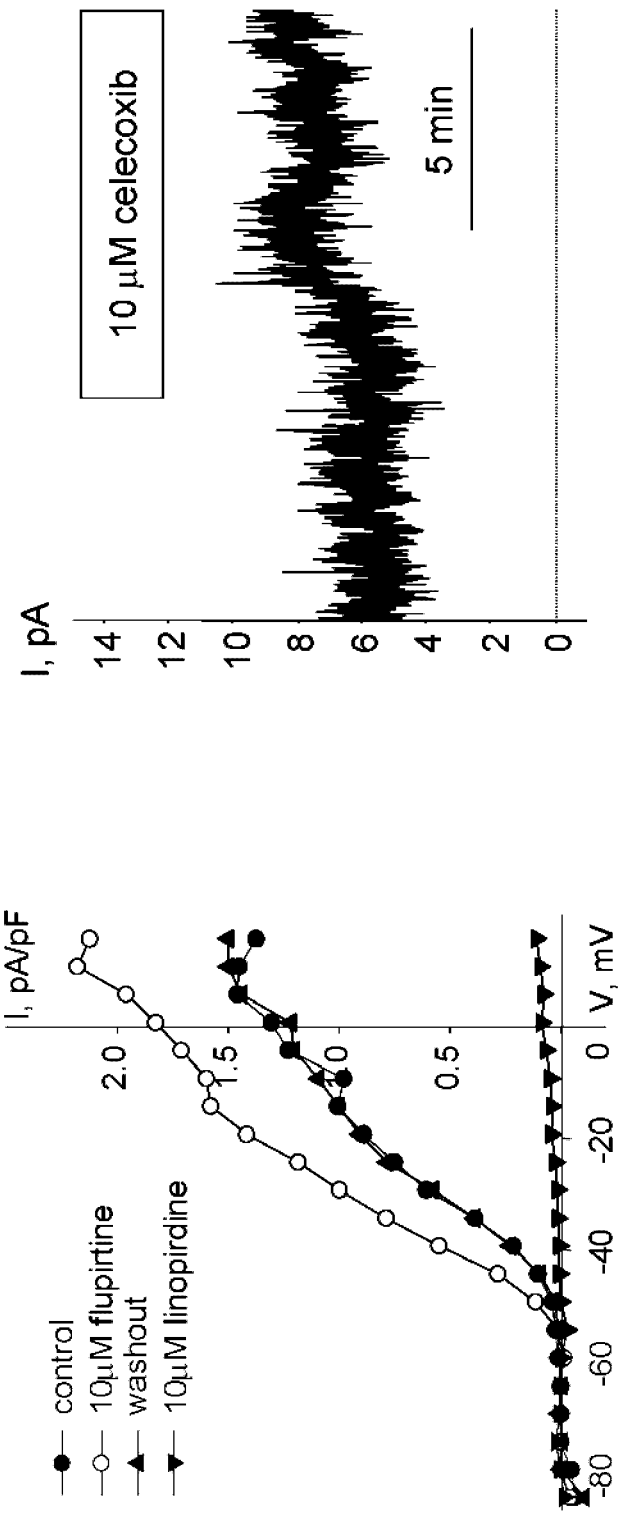
Figure 8:
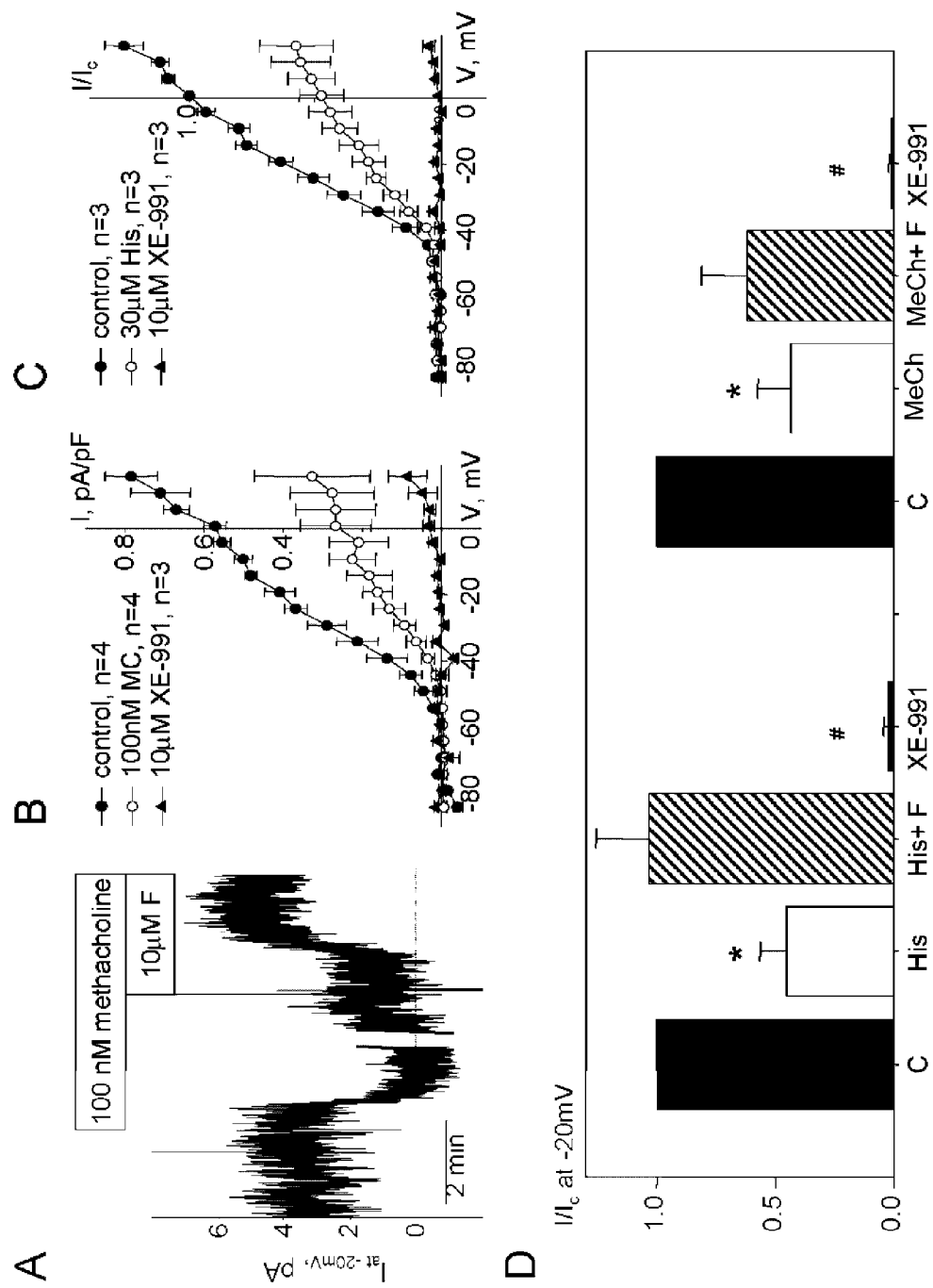
FIG. 8 contains four graphs evidenced that suppression of Kv7 currents in ASMCs by bronchoconstrictor agonists is reversed by the Kv7 channel activator flupirtine.

Another investigation relating to this aspect of the invention was directed to investigating Kv7 currents in freshly dissociated guinea pig ASMCs. Using methods described by Janssen et al., "Acetylcholine activates non-selective cation and chloride conductances in canine and guinea-pig tracheal myocytes," J. Physiol 453, p. 197-218 (1992), ASMCs were isolated from guinea pig bronchioles by enzymatic digestion and whole cell perforated patch clamp electrophysiology was used to record Kv7 currents. Kv7 currents were recorded in isolation from other ionic currents by including 100 μM gadolinium chloride in the external solution and applying relatively long (about five second) voltage steps, during which many other classes of channels inactivate. These methods were pioneered for the recording of Kv7 currents in VSMCs, and are reported in Mackie et al., "Vascular KCNQ potassium channels as novel targets for the control of mesenteric artery constriction by vasopressin, based on studies in single cells, pressurized arteries, and in vivo measurements of mesenteric vascular resistance," Journal of Pharmacology and Experimental Therapeutics 325: 475-483 (2008), and Brueggemann et al., "Vasopressin stimulates action potential firing by protein kinase C-dependent inhibition of KCNQ5 in A7r5 rat aortic smooth muscle cells," Am J Physiol Heart Circ Physiol 292(3):H1352-H1363 (2007). The currents recorded from ASMCs were larger than their VSMC counterparts, but otherwise very similar, having all the expected characteristics of Kv7 currents, including: slow kinetics of activation with no apparent inactivation during a 5s voltage step (FIG. 4); voltage-dependent activation with a threshold negative to −60 mV and a $V_{0.5}$ of approximately −34 mV (FIG. 5); reversible enhancement by the selective Kv7 channel activator flupirtine (FIG. 6); complete suppression by the selective Kv7 channel blockers linopirdine and XE991 (FIGS. 6 and 8). Preliminary studies also showed that the ASMC Kv7 currents were enhanced by celecoxib (FIG. 7), but not by diclofenac, similar to what has been observed for VSMC Kv7 currents, reported in Brueggemann et al., "Differential Effects of Selective COX-2 Inhibitors on Vascular Smooth Muscle Ion Channels May Account for Differences in Cardiovascular Risk Profiles," Molecular Pharmacology 76: 1053-1061 (2009).

A third investigation relating to this aspect of the invention was directed to the suppression of Kv7 currents by bronchoconstrictor agonists and its reversal by Kv7 channel activators. In initial studies the effects of two known bronchoconstrictors, methacholine (100 nM) and histamine (30 μM) were tested. Both significantly suppressed Kv7 currents in guinea pig ASMCs (FIG. 8), but the Kv7 channel activator flupirtine was effective in restoring the currents to near control levels in both cases (FIGS. 8A and 8D). FIG. 8A shows a representative time course of Kv7 current recorded at a holding voltage of −20 mV. Red lines indicate a 10 minute break in recording. Kv7 currents were completely suppressed by 100 nM methacholine and this was fully reversed by addition of 10 μM flupirtine (F). FIG. 8B shows mean current-voltage (I-V) curves recorded before, during treatment with 100 nM methacholine (MeCh), and after addition of 10 μM XE-991. FIG. 8C, shows mean I-V curves recorded before, during treatment with 30 μM histamine (His), and after addition of 10 μM XE-991. FIG. 8D shows summarized effects of treatments on Kv7 currents measured at −20 mV (C=control; His=30 μM histamine; F=10 μM flupirtine; MeCh=100 nM methacholine). A significant difference from control is indicated by * ($p<0.05$) and # ($p<0.01$), paired Student's t-test.

The results described above have important relevance to asthma, as they address novel mechanisms that may contribute to the development of asthma, for example, suppression of Kv7 currents by inflammatory mediators, or altered expression and function of Kv7 channels, leading to ASMC contraction and airway narrowing. The results also indicate the existence of innovative approaches to the treatment of asthma, including the testing of new pharmacological strategies that are rationally designed to provide relief of airway constriction. On the basis of the above, it was hypothesized that Kv7 channels play an important role in setting resting membrane voltage in ASMCs and that the activity of these channels is suppressed by ASMC agonists that induce airway narrowing. It was further hypothesized that pharmacological agents that activate these channels will be effective bronchodilators that may be used therapeutically in the treatment of asthma and/or other airway diseases.

In view of the above and the following investigations, an aspect of the present invention is a method of treating a bronchospastic condition, for example, asthma, that can lead to airway obstruction in a patient. The method includes administering a pharmaceutical to the patient in a therapeutic amount sufficient to activate the Kv7 potassium channels of an airway smooth muscle cell. The pharmaceutical comprises at least one KCNQ channel activator. The pharmaceutical may also be combined with one or more other pharmaceuticals for other classes of bronchodilators, for example, a $\beta_2$-adrenergic receptor agonist. The pharmaceutical is preferably administered by inhalation. However, other routes of administration are potentially possible such as oral or intravenous. In the case of a combination pharmaceutical, the term "administration" refers to both concurrent and sequential administration of the active agents.

An additional aspect of the present invention is a combination pharmaceutical comprising both at least one KCNQ channel activator and at least one $\beta_2$-adrenergic receptor agonist. Suitable examples of KCNQ channel activators include retigabine, flupirtine, and celecoxib and its analogs (2,5-dimethylcelecoxib, as a nonlimiting example). Nonlimiting examples of suitable $\beta_2$-adrenergic receptor agonists include formoterol fumarate (hereinafter, formoterol or FF), albuterol (salbutamol), and terbutaline. The structure, composition, and manufacture of these KCNQ channel activators and $\beta_2$-adrenergic receptor agonists are well known in the art and therefore will not be explained further herein. The pharmaceutical, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

The dose of the pharmaceutical administered to an animal, particularly a human, in the context of the present invention, should be sufficient to effect a therapeutic response in the animal over a reasonable time frame. One skilled in the art will recognize that dosage will depend upon a variety of factors including a condition of the animal, the body weight of the animal, the nature and extent of the symptoms, the kind of concurrent treatment, the frequency of treatment, etc. The size of the dose also will be determined by the route, timing and frequency of administration as well as the existence, nature, and extent of any adverse side effects that might accompany the administration of the pharmaceutical and the desired physiological effect. Appropriate dosing may be determined empirically from clinical trials, starting with doses that have established safety profiles when used for other applications (e.g., doses of flupirtine used to treat fibromyalgia pain or doses of retigabine used to treat epilepsy).

Figure 9:
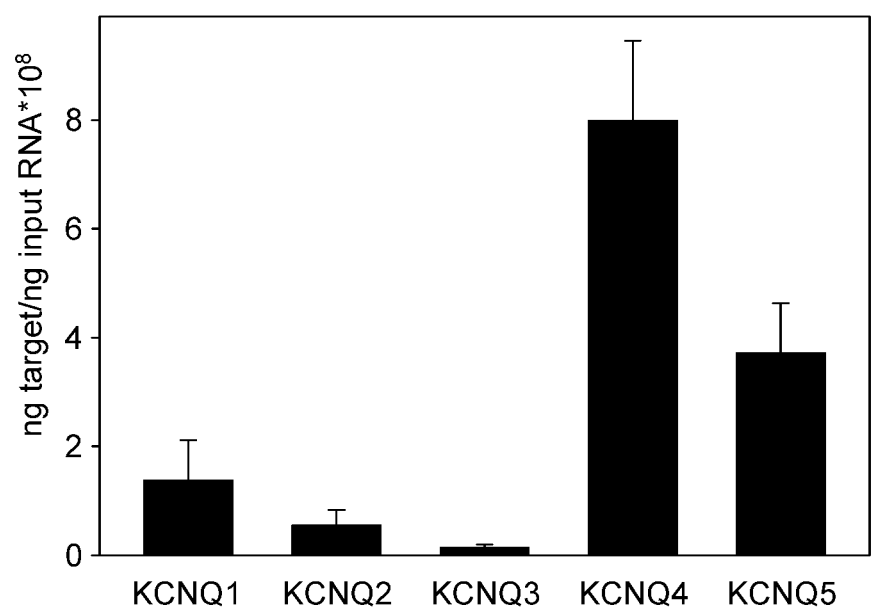
FIG. 9 is a bar graph representing multiple KCNQ subtypes that are expressed in rat airway smooth muscle cells (ASMCs). Expression levels of mRNAs for KCNQ1-5 were estimated using quantitative RT-PCR in rat airway myocytes.

An investigation relating to these aspects of the invention was conducted to determine whether KCNQ (Kv7) K$^+$ channels are expressed and functional in rat airway myocytes. To accomplish this, a combination of real time polymerase chain reaction (RT-PCR) and patch-clamp electrophysiology was used. Isolation of rat ASMCs from bronchial strips for the patch-clamp electrophysiology as well as RNA isolation from rat trachea for the RT-PCR were performed using methods as described in Brueggemann et al., "KCNQ (Kv7) potassium channel activators as bronchodilators: combination with a $\beta_2$-adrenergic agonist enhances relaxation of rat airways," Am J Physiol Lung Cell Mol Physiol (in press), incorporated herein by reference. Using quantitative RT-PCR, mRNAs for all five mammalian KCNQ subtypes (KCNQ1-5) were detected in cells isolated from rat tracheal smooth muscle strips. Based on mean expression data from n=4 rats, this relatively pure population of ASMCs expresses KCNQ4>KCNQ5>KCNQ1>KCNQ2>KCNQ3, as represented in FIG. 9.

Figure 10:
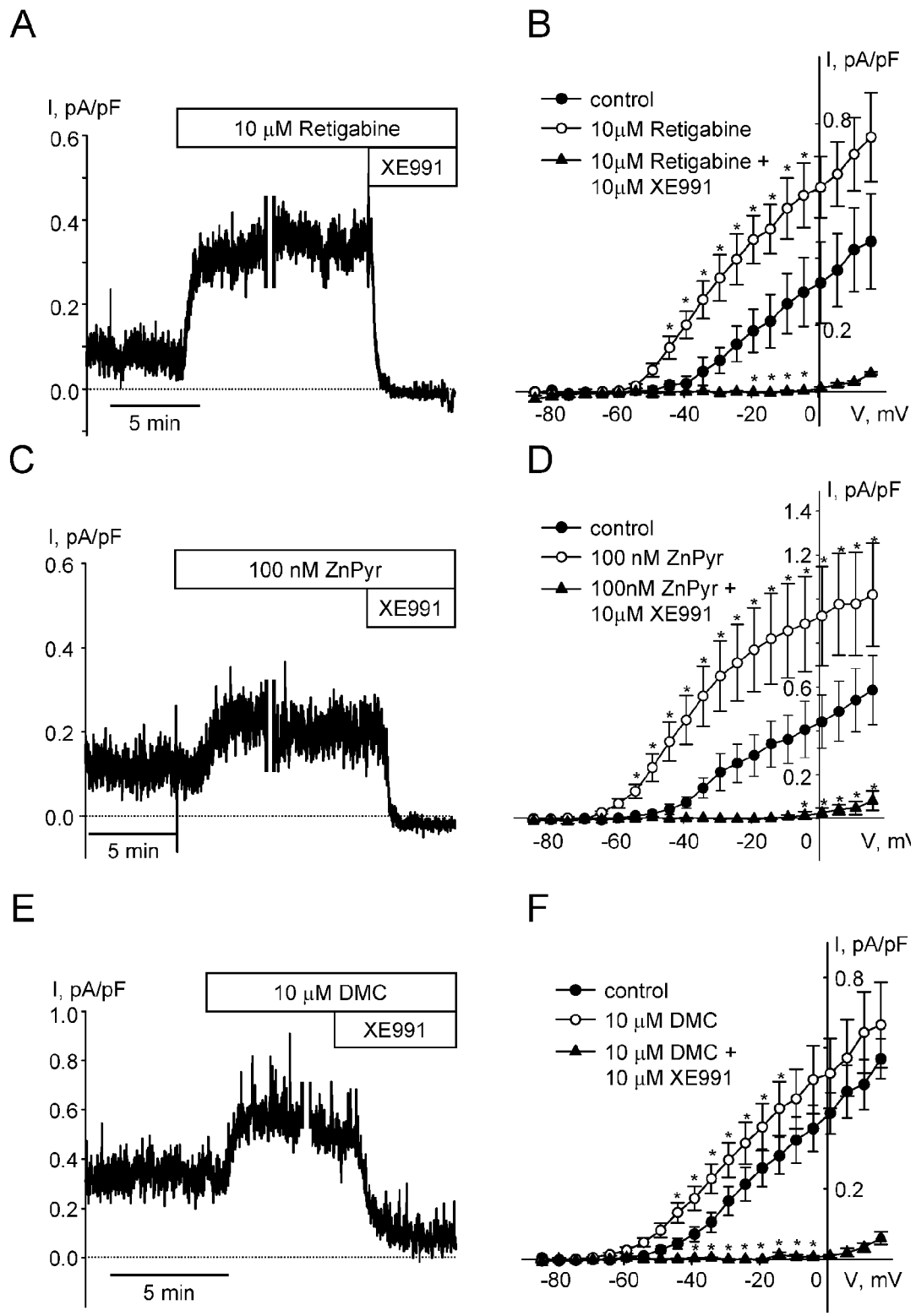
FIGS. 10A-F are plots representing pharmacology of KCNQ currents in rat ASMCs. Retigabine, Zinc pyrithione (ZnPyr), and 2,5-dimethylcelecoxib (DMC) are established KCNQ channel activators.

Functional expression of KCNQ channels was definitively determined by measuring K$^+$ currents with the expected electrophysiological and pharmacological characteristics. Therefore K$^+$ currents in enzymatically dispersed rat airway myocytes were measured using patch-clamp electrophysiology. Non-inactivating K$^+$ currents recorded at −20 mV holding voltage in rat ASMCs were enhanced in the presence of selective KCNQ channel activators retigabine (10 μM) and zinc pyrithione (ZnPyr, 100 nM) and inhibited upon application of the KCNQ channel blocker XE991 (10 μM), indicating that sustained current at that voltage was predominantly mediated by KCNQ channels (FIG. 10A,C). Using a voltage step protocol, both retigabine and ZnPyr increased KCNQ currents recorded at voltages positive to −40 mV and shifted the threshold of channel activation to more negative voltages (FIG. 10B,D). 2,5-dimethylcelecoxib (DMC), a structural analog of the cyclooxygenase-2 inhibitor, celecoxib, acts as a KCNQ channel activator (similar to celecoxib) in vascular smooth muscle cells and guinea pig ASMCs. It was found that DMC is also effective as an activator of KCNQ currents in rat ASMCs (FIG. 10E,F).

Figure 11:
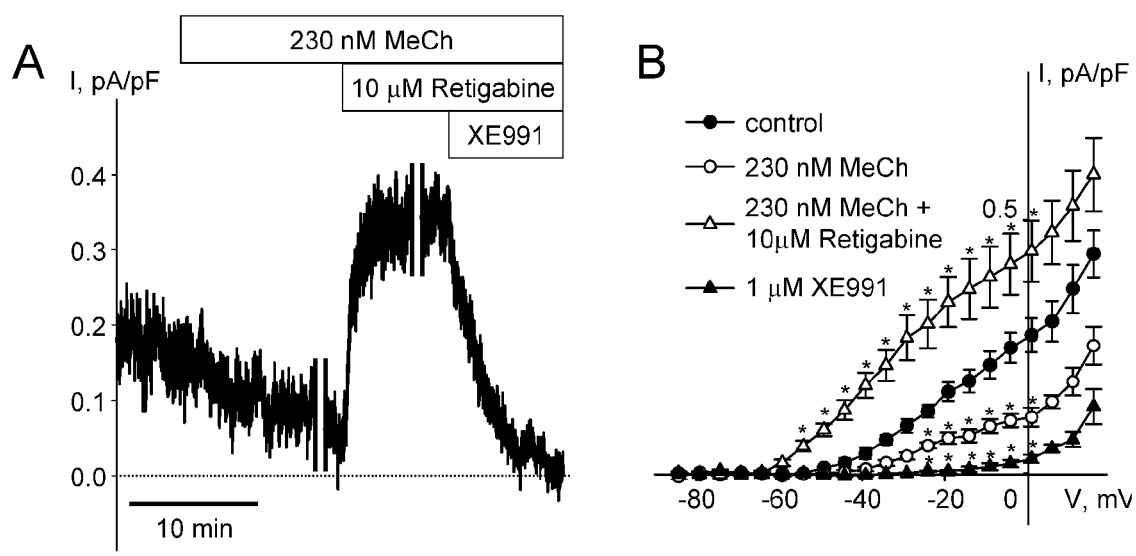
FIGS. 11A and 11B are plots representing suppression of KCNQ currents by methacholine (MeCh) in rat ASMCs and their restoration by the KCNQ channel activator retigabine.

Treatment with the muscarinic cholinergic agonist methacholine (MeCh, 230 nM) significantly reduced KCNQ currents recorded at −20 mV holding voltage in rat ASMCs (55.1±6.2% reduction, n=7, P<0.05, paired t-test), in agreement with the previous finding in guinea pig ASMCs. Application of retigabine (10 μM) in the continued presence of MeCh (230 nM) more than fully restored the currents, resulting in an increase in current amplitude to greater than the control level; the currents were completely abolished on subsequent application of XE991 (1 μM) (FIG. 11). FIG. 11A shows a representative time course of KCNQ current inhibition during treatment of an ASMC (C=20.0 pF) with MeCh (230 nM for 20 minutes), recorded in an ASMC at −20 mV holding voltage. After 10 minutes of MeCh treatment, the time course recording was interrupted for 10 minutes for measurement of steady-state I-V relationship (time break indicated by vertical gray lines). Then, after an additional one minute recording at −20 mV holding voltage, retigabine (10 μM) was applied in the presence of MeCh for 5 minutes. The time course recording was interrupted again for ten minutes for measurement of steady-state I-V relationship and, after an additional one minute time course recording, XE991 (1 μM) was applied in the presence of MeCh and retigabine for ten minutes. FIG. 11B shows I-V relationships of KCNQ currents recorded in ASMCs before (control, filled circles, n=7), during treatment with 230 nM MeCh (open circles, n=7), in the presence of retigabine (10 µM) applied with 230 nM MeCh (open triangles, n=7), and in the presence of XE991 (1 µM, filled triangles, n=7). An asterisk * indicates a significant difference from control (One Way Repeated Measures ANOVA, p<0.05).

Figure 12:
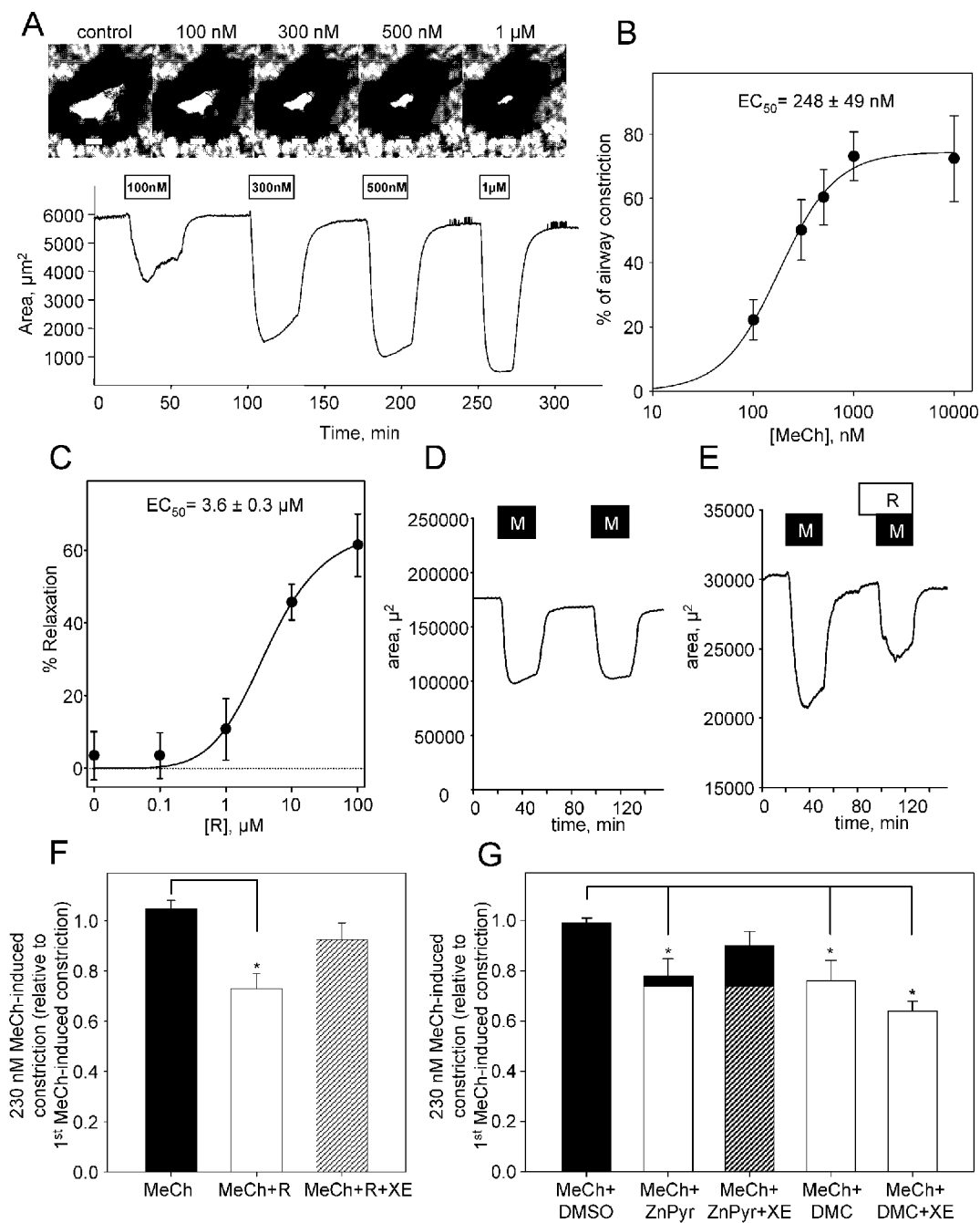
FIGS. 12A-G are images and charts representing the attenuation of MeCh-induced airway constriction by KCNQ $K^+$ channels activators.

Another investigation was performed to investigate the ability of KCNQ channel activators to attenuate MeCh-induced concentration-dependent constriction of rat bronchioles in precision-cut lung slices (PCLS). The PCLS were prepared using methods described by Brueggemann et al., "KCNQ (Kv7) potassium channel activators as bronchodilators: combination with a $\beta_2$-adrenergic agonist enhances relaxation of rat airways," Am J Physiol Lung Cell Mol Physiol (in press). PCLS were superfused with increasing concentrations of MeCh in the range from 100 nM to 1 µM. Each concentration was applied for thirty minutes, followed by a forty-five minute washout prior to application of the next MeCh concentration (FIG. 12A,B). FIG. 12A shows (Top) representative images of a small airway before treatment (control) and in the presence of MeCh at increasing concentrations (100 nM, 300 nM, 500 nM, 1 µM) and (Bottom) corresponding representative time course of changes in lumenal area of the same small airway. Percent of airway constriction, relative to the cross-sectional area measured before the initial MeCh treatment, was calculated for each MeCh concentration and plotted against concentration of MeCh. Concentration-response curves for each experiment were fitted by the Hill equation with a mean $EC_{50}$ of 248±49 nM, Hill coefficient of 1.6±0.2, and maximal constriction of 81±7% (n=5, FIG. 12B).

Retigabine was observed to induce dose-dependent sustained relaxation of airways pre-constricted for thirty minutes with 230 nM MeCh ($EC_{50}$=3.6±0.3 µM; maximum relaxation 61±9%, FIG. 12C). Bronchorelaxant effects were further assessed by measuring the extent of bronchoconstriction when MeCh was applied in the absence or presence of different structurally unrelated KCNQ channel activators (or vehicle). Application of 230 nM MeCh produced similar degrees of airway constriction on repetitive exposures (FIG. 12D). FIG. 12E shows a representative time course of changes in lumenal area of a small airway on application of 230 nM MeCh followed by a thirty-minute washout, fifteen-minute application of retigabine (R, 10 µM) alone, and then a second application of 230 nM MeCh for thirty minutes in the presence of retigabine (10 µM). MeCh-induced airway constriction was reduced by about 31% in the presence of 10 µM retigabine ("MeCh+R," n=8, FIG. 12E,F). FIG. 12G is a summarized bar graph of second MeCh-induced constriction relative to first MeCh-induced constriction when MeCh (230 nM) was applied in the presence of a vehicle (0.1% of DMSO, "MeCh+DMSO" (black bar), n=5), in the presence of ZnPyr (1 µM, "MeCh+ZnPyr" (dark grey bar), n=6), in the presence of ZnPyr (1 µM) together with XE991 (10 µM, "MeCh+ZnPyr+XE" (dark grey striped bar), n=5), in the presence of DMC (10 µM, "MeCh+DMC" (light grey bar), n=6), and in the presence of DMC (10 µM) together with XE991 (10 µM, "MeCh+DMC+XE" (light grey striped bar), n=5). DMC and ZnPyr also significantly attenuated MeCh-induced airway constriction relative to vehicle controls: 10 µM DMC by 23% ("MeCh+DMC," n=6); 1 µM ZnPyr by 21% ("MeCh+ZnPyr," n=6) (FIG. 12G). The actions of both retigabine and ZnPyr were suppressed or prevented by inclusion of the KCNQ channel blocker XE991 (10 µM) ("MeCh+R+XE" in FIG. 12F; "MeCh+ZnPyr+XE" in FIG. 12G), providing evidence for the specific targeting of KCNQ channels to elicit their bronchorelaxant effects. The bronchorelaxant effects of 2,5-dimethylcelecoxib were not significantly reduced in the presence of XE991 (FIG. 12F).

Figure 13:
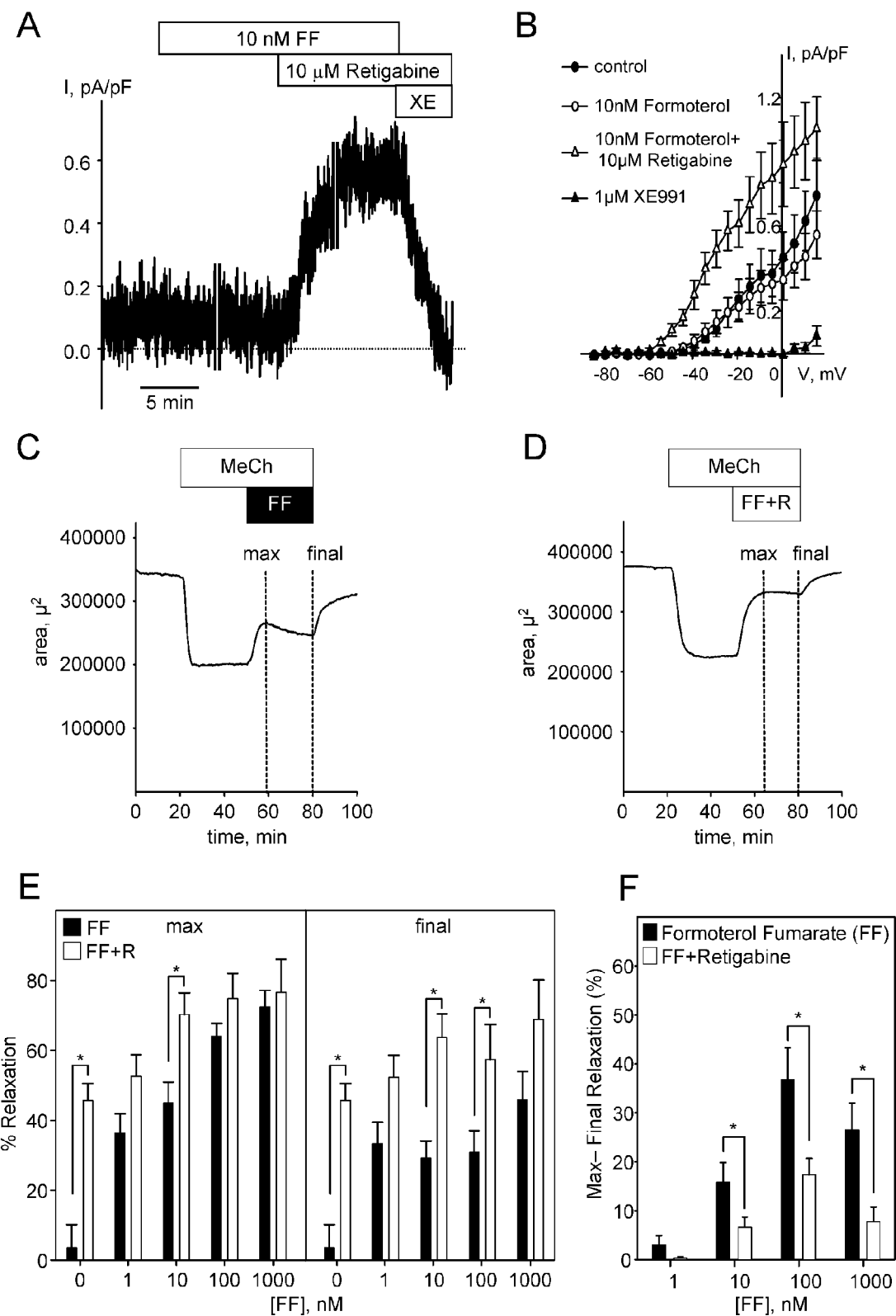
FIGS. 13A-F are plots representing effects of formoterol fumarate (FF) on KCNQ currents and on relaxation of rat airways, wherein no detectable effects were observed on KCNQ currents, but enhanced bronchodilator responses were observed when formoterol fumarate was combined with retigabine (FF+R).

Based on the above findings, an additional investigation was conducted to investigate potential combination therapies for the treatment of asthma. $\beta_2$-adrenergic receptor agonists are commonly used for bronchodilator therapy. The investigation examined whether the bronchorelaxant effects of long-acting $\beta_2$-adrenergic receptor agonist, formoterol, were mediated via activation of KCNQ channels in rat airway myocytes. FIG. 13A is a representative time course of KCNQ current recording in an ASMC (C=13.9 pF) at −20 mV holding voltage before (5 minutes) and during treatment with formoterol (10 nM FF for 5 minutes). The time course recording was interrupted for 10 minutes for measurement of steady-state I-V relationship (time break indicated by vertical gray lines). After an additional 5 minutes recording, retigabine (10 µM) was applied in the continued presence of formoterol. The time course recording was interrupted again for 10 minutes for recording of steady-state I-V curves, and, after an additional 5 minutes recording, XE991 (1 µM) was applied in the presence of retigabine. FIG. 13B shows I-V relationships of KCNQ currents recorded in ASMCs before (control, filled circles, n=4), during treatment with 10 nM formoterol (open circles, n=4), in the presence of retigabine (10 µM) applied with 10 nM formoterol (open triangles, n=3), and in the presence of XE991 (1 µM, filled triangles, n=3). These results show that formoterol (10 nM), at a concentration sufficient to produce significant relaxation of rat airways, did not enhance KCNQ currents recorded at −20 mV holding voltage in rat ASMCs (FIG. 13A,B). However, subsequent application of retigabine (10 µM) in the presence of formoterol significantly increased the current and the current was effectively abolished by application of 1 µM of XE991 (FIG. 13A,B). Another β-adrenergic receptor agonist, isoproterenol (100 nM), was also ineffective in enhancement of KCNQ currents (data not shown).

FIG. 13C is a representative time course of changes in lumenal area of a small airway in rat PCLS on application of 230 nM MeCh (thirty minutes) followed by application of 230 nM MeCh in the presence of 10 nM formoterol (FF, thirty minutes). Dashed vertical lines marked "max" and "final" indicate 1 minute time intervals where the maximum or final relaxation was measured relative to the MeCh-induced constriction (measured during the last minute of MeCh alone). FIG. 13D is a representative time course of changes in lumenal area of a small airway treated as in panel C, except that 10 µM retigabine was included with the formoterol treatment ("FF+R," thirty minutes). FIG. 13E is a summarized bar graph of formoterol-induced relaxation, with or without 10 µM retigabine (black or grey bars, respectively), measured at the "max" and "final" time points as indicated on FIGS. 13C and 13D (n=6-10). FIG. 13F is a summarized bar graph of the maximum minus the final percent relaxation depicted in FIG. 13E. An asterisk * indicates a significant difference between formoterol treatments alone versus formoterol plus retigabine treatments (Student's t-test, n=6-10, P<0.05).

These results show that in rat PCLS, formoterol (1-1000 nM) induced concentration-dependent relaxation of airways constricted with 230 nM MeCh, to a maximum of 72±5% at 1 µM (FIG. 13E). However, there was a noticeable time-dependent decline in the relaxation response at concentrations of formoterol greater than or equal to 10 nM (compare maximal relaxation to final relaxation in FIG. 13C,E). The combination of varying concentrations of formoterol with a submaximal concentration of retigabine was then tested (10 µM, a concentration that produced 45.7±4.9% relaxation when applied alone; FIG. 12C). In the presence of retigabine, both maximum and sustained airway relaxation were increased relative to formoterol alone (FIG. 13E). Importantly, there was a notable reduction in time dependent desensitization to formoterol when it was combined with retigabine (FIG. 13D). The amount of desensitization for each concentration of formoterol in the absence and presence of 10 μM retigabine was estimated by subtraction of final relaxation (after thirty-minute treatment) from maximal relaxation. Desensitization to formoterol (10-1000 nM) was significantly decreased in the presence of 10 μM retigabine (FIG. 13F).

Figure 14:
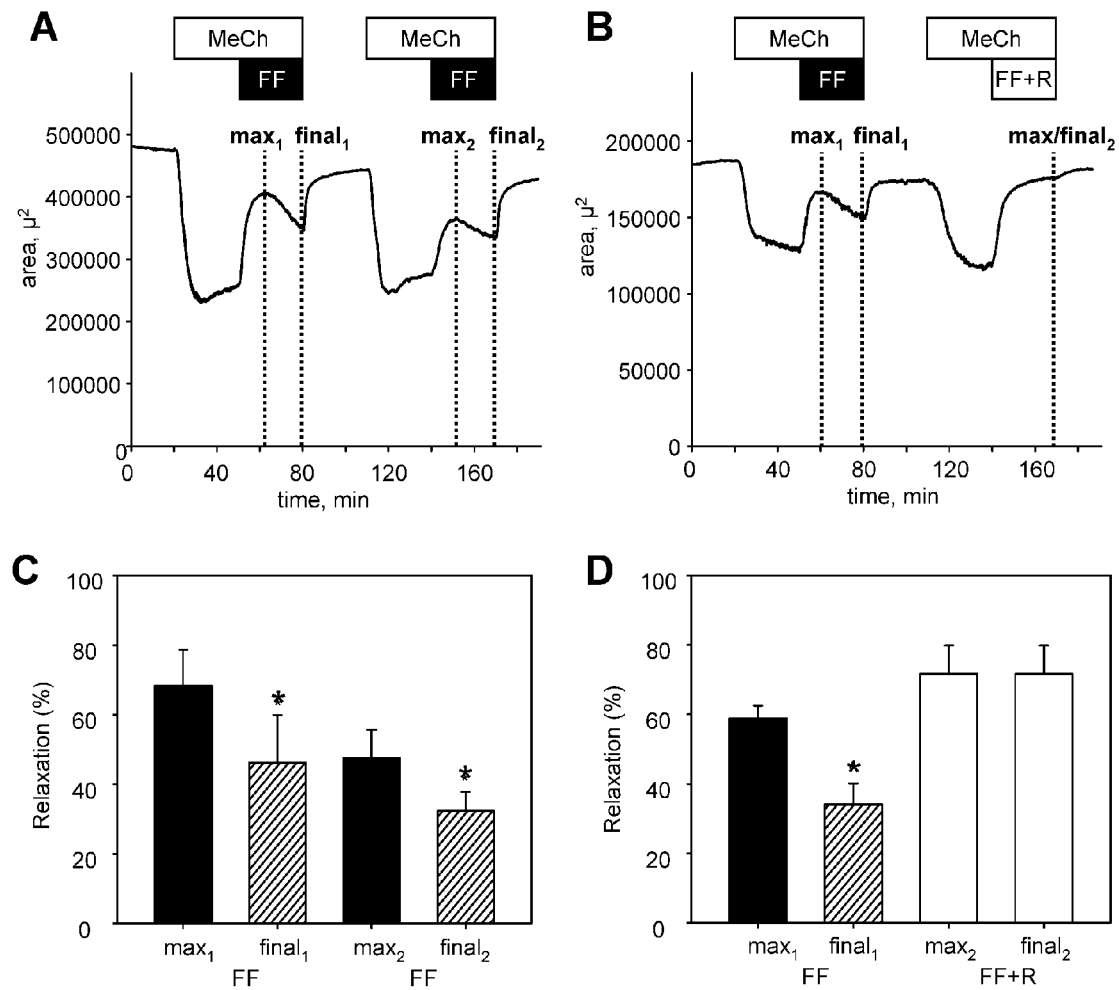
FIGS. 14A-D are graphs representing the ability for combinations of retigabine with formoterol fumarate to suppress desensitization in airway relaxation responses.

To further investigate the desensitization to formoterol in rat PCLS, formoterol (10 nM) was applied twice, at a 90 minute interval, to airways constricted repetitively with 230 nM MeCh. As observed previously, formoterol (10 nM, thirty-minute) induced acute relaxation of airways constricted with 230 nM MeCh, peaking at 68±10%, but declining significantly to a final relaxation of only 46±14% after thirty minutes of formoterol treatment (FIG. 14A,C). After washout of both MeCh and formoterol, a second application of MeCh produced an airway constriction of comparable magnitude to the initial application, whereas formoterol-induced relaxation was reduced on the second application (peak relaxation declined from 68±10% to 48±8% and final relaxation declined from 46±14% to 32±6%, FIG. 14A,C). When retigabine (10 μM) was combined with the second application of formoterol there was a significantly greater relaxation without any detectable time dependent desensitization (72±8% peak and 72±8% final relaxation after thirty minutes with combined formoterol and retigabine treatment, compared with only 59±4% peak relaxation and 34±6% final relaxation when the same slices were exposed acutely to formoterol alone, FIG. 14B,D).

Figure 15:
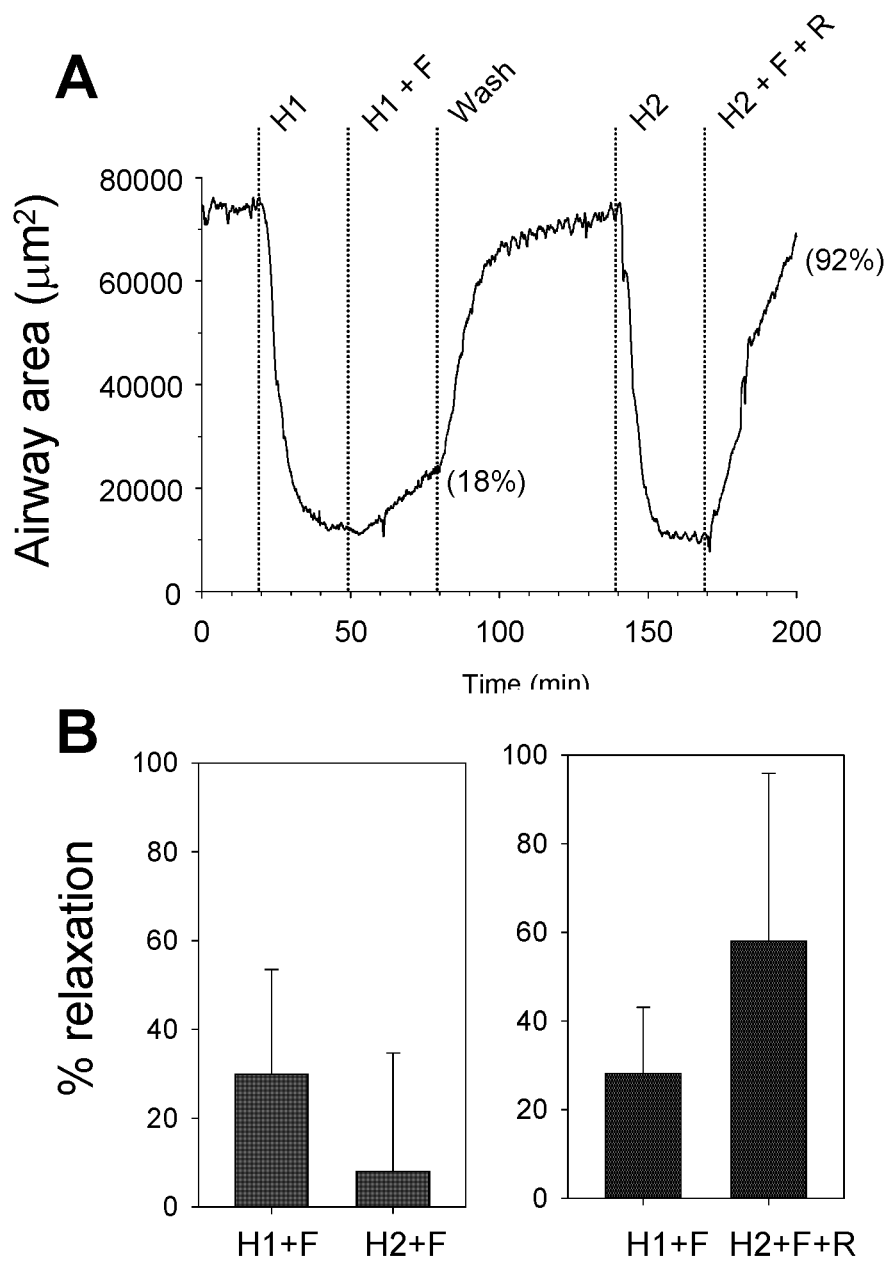
FIGS. 15A and 15B are graphs representing results of a combination therapy comprising Kv7 channel activator retigabine and formoterol fumarate which were observed to enhance relaxation of human asthmatic airway.

Testing following similar procedures as those described above was performed on human PCLS, including slices from an asthmatic human lung (the patient died from an asthmatic attack; FIG. 15A). FIG. 15A is a representative recording of airway area from a PCLS derived from an asthmatic human lung. Histamine (25 pM) was applied twice (H1 & H2), followed by a thirty-minute treatment with 30 pM formoterol alone ("H1+F"; 18% relaxation) or 30 pM formoterol plus 30 μM retigabine ("H2+F+R"; 92% relaxation). FIG. 15B shows summarized results from human PCLS exposed to two consecutive treatments with 50 nM histamine (H1 and H2), the first with relaxation by formoterol alone (10 pM), and the second with either 10 pM formoterol alone (left) or 10 pM formoterol plus 10 μM retigabine (right). These tests obtained similar results to the rat PCLS, supporting the feasibility of this combination therapy for humans. A major advantage of human PCLS over other types of in vitro studies is that this preparation contains all of the cell types present in the organ in vivo, in their normal spatial relationships, and with the potential for normal intercellular communication and cellular interactions. As stated in "In Vitro Lung Slices: A Powerful Approach for Assessment of Lung Pathophysiology," Liberati et al, Expert Rev. Mol. Diagn., 501-508 (2010), "one of the best arguments for the use of this in vitro human lung system is that it allows for comparison between human and animal and possible better extrapolation to the human in vivo situation." It is believed that the human lung slice investigations described herein provide an accurate prediction of the activity of combination therapy in vivo.

Figure 16:
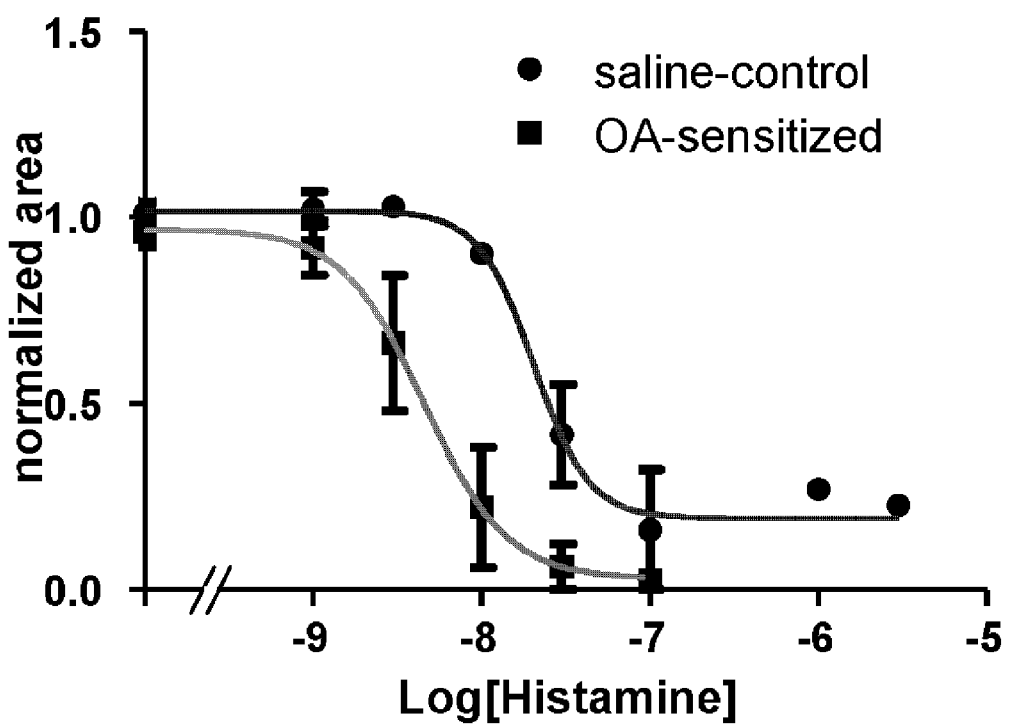
FIG. 16 is a graph showing dose-response curves for histamine-induced airway constriction in precision-cut lung slices (PCLS) from control or ovalbumin-sensitized guinea pigs, normalized to initial airway area.

To assess the feasibility of inhalational therapy with a Kv7 channel activator, an investigation was conducted to assess the ability of retigabine to exert a therapeutic anti-bronchospastic benefit in vivo. It is common in the art to use guinea pigs as an animal model of early, "immediate-type" allergic bronchoconstriction and bronchial hyperresponsiveness. This model involves a series of three intraperitoneal injections of ovalbumin (OA) or saline (as control) over a one week period, followed by a two-week sensitization period, and finally challenge with aerosolized ovalbumin. In preliminary studies, this protocol has uniformly elicited severe respiratory attacks in ovalbumin-sensitized guinea pigs (but not saline control animals) exposed to ovalbumin, with symptoms including rapid breathing, then labored breathing, prolonged expiration, gasping, coughing, dilation of alae nasi, and finally cyanosis and convulsion. In PCLS from ovalbumin-sensitized guinea pigs, ovalbumin induced profound constriction of airways, but ovalbumin had little or no effect on airways in PCLs from saline control animals. Airway hyperresponsiveness (AHR) was confirmed in PCLS from ovalbumin-sensitized guinea pigs, which were significantly more sensitive to histamine (FIG. 16) and methacholine (not shown).

In the investigation, two saline-control and two ovalbumin-sensitized animals were exposed to aerosolized ovalbumin on three consecutive days, but in this case the ovalbumin treatment was administered with varying doses of retigabine on consecutive days. A thirty-minute exposure to ovalbumin, with varying doses of retigabine up to 1 mM, had no apparent effect on saline control animals. In contrast, ovalbumin with 0, 10, or 100 μM retigabine induced severe asthmatic attacks in the ovalbumin-sensitized guinea pigs (the animals were convulsing and had to be removed from the chamber within fifteen minutes and each took more than an hour to exhibit a normal breathing pattern and recover from cyanosis), whereas when the same guinea pigs were exposed to a mix of aerosolized ovalbumin and 1 mM retigabine, the respiratory symptoms were almost completely abrogated (the animals were removed from the chamber after the full thirty-minute treatment and appeared to be fully recovered within a few minutes). This investigation supports the feasibility of inhalational therapy with a Kv7 channel activator for relief of immediate-type allergic bronchoconstriction and bronchial hyperresponsiveness.

Bronchial hyperresponsiveness in asthma is attributed in part to excessive $G_{q/11}$-coupled receptor activation. The apparent involvement of L-type VSCCs in airway constriction and $G_{q/11}$-coupled bronchoconstrictor signal transduction led to a number of clinical trials of CCBs to limit excessive bronchoconstriction in asthma patients. Unfortunately, these trials produced inconsistent results. Although CCBs were effective in relieving airway hyperconstriction in a subset of patients in most of the clinical trials, COB therapy for asthma was ultimately abandoned due to adverse side effects and limitations of formulation that prevented effective inhalational administration of the commonly used CCBs, such as verapamil and nifedipine. Like CCBs, KCNQ channel activators were developed for clinical use in the treatment of conditions unrelated to airway diseases, predominantly neurological conditions such as epilepsy and pain. The above investigations support an alternative use for KCNQ channel activators as bronchodilators. These drugs may be more amenable to the development of inhalational formulations or more selective agents may be identified that can be administered systemically to activate primarily the ASMC KCNQ channels and avoid unwanted off-target effects.

Evseev et al., "Functional effects of KCNQ $K^+$ channels in airway smooth muscle," Front Physiol 4, (2013), recently tested the effect of inhaled retigabine on MeCh-induced bronchoconstriction in conscious mice and observed a significant albeit transient bronchorelaxant effect. It should be noted that a number of species differences in bronchoconstrictor pathways have been reported previously. For example, murine airway smooth muscle is known to be less responsive to asthma-related bronchoconstrictors, such as histamine and leukotrienes, than is airway smooth muscle in other species. And, unlike human airways, allergen-induced bronchoconstriction is mediated primarily by serotonin in both murine and rat airways. Despite these differences, it is clear that the fundamental $Ca^{2+}$-dependent contraction of ASMCs is a common downstream determinant of airway diameter across mammalian species and that KCNQ channel activators have demonstrated bronchorelaxant effects, at least in vitro, in all mammalian species tested to date.

$\beta_2$-adrenergic receptor agonists are commonly used therapeutically for the relief of excessive airway constriction. Their bronchorelaxant mechanism involves increased formation of cyclic adenosine monophosphate and activation of protein kinase A, which then phosphorylates key regulatory proteins involved in the control of airway smooth muscle tone. Activation of $BK_{Ca}$ $K^+$ channels has been proposed as one of the downstream effector pathways, though the possibility that KCNQ channel activation is also involved has not previously been explored. There is evidence in the art that $\beta$-adrenergic receptor activation can enhance KCNQ1 channel activity in cardiac myocytes and activation of KCNQ4 channels has been proposed as an essential mechanism in the vasorelaxant effects of the $\beta$-adrenergic receptor agonist isoproterenol in rat renal arteries. The above investigations argue against a role of KCNQ channels in the bronchorelaxant effects of $\beta_2$-adrenergic receptor activation, as no effect of $\beta_2$-adrenergic agonists on ASMC KCNQ currents was observed at concentrations that were effective in relaxation of rat bronchioles.

Sustained or repetitive exposure to $\beta_2$-adrenergic receptor agonists is known to induce receptor desensitization, which represents a limitation for the therapeutic use of these drugs for the relief of asthmatic attacks. The above investigations bore this out in the reduced rat airway relaxation responses to sustained or repetitive exposures to formoterol. Notably, combining retigabine with formoterol mitigated the apparent desensitization. A possible explanation for this is that, while $BK_{Ca}$ channel activation would fully depend on activity of a $\beta_2$-adrenergic receptor and thus would be reduced upon $\beta_2$-adrenoceptor desensitization, activity of KCNQ channels would not be affected by the loss of $\beta_2$-adrenoceptor signaling. Thus, whereas activation of KCNQ channels may be redundant when $\beta_2$-adrenergic receptors are fully able to activate $BK_{Ca}$ channels, when the latter response is reduced by $\beta_2$-adrenergic receptor desensitization, the activation of KCNQ channels may be more prominent and sufficient to sustain bronchorelaxation on its own.

In summary, the above investigations suggest that KCNQ channel activators, which are already in clinical use for other conditions, may be re-purposed as promising new bronchodilator therapies. Previous studies in the art have demonstrated that there are a number of added benefits in using combinations of $\beta_2$-adrenergic agonists and anti-muscarinic agents for the treatment of airway diseases. Considering the findings reported herein that KCNQ channel activation can oppose both muscarinic and histaminergic bronchoconstriction (FIGS. 13 and 14), it was concluded that a combination of KCNQ channel activators with $\beta_2$ agonists may be even more beneficial. The investigations herein provide the first evidence that such combination therapy might indeed provide a more effective bronchorelaxant effect than either treatment alone.

While the invention has been described in terms of specific embodiments, it is apparent that the underlying discoveries and teachings presented herein could be adopted by those skilled in the art for uses beyond those suggested herein. Therefore, the scope of the invention is to be limited only by the following claims.

The invention claimed is:

1. A combination pharmaceutical comprising:
   at least one $\beta$-adrenergic receptor agonist, wherein sustained or repetitive exposure by a subject to the $\beta$-adrenergic receptor agonist induces receptor desensitization in the subject; and
   at least one composition that activates Kv7 potassium channels of a lipid membrane of an airway smooth muscle cell;
   wherein the combination of the $\beta$-adrenergic receptor agonist and the composition mitigates the effects of the receptor desensitization induced by the $\beta$-adrenergic receptor agonist.

2. The combination pharmaceutical of claim 1, wherein the effect of the composition is to activate the Kv7 potassium channels.

3. The combination pharmaceutical of claim 1, wherein the composition comprises a compound chosen from the group consisting of retigabine, zinc pyrithione, flupirtine, celecoxib, dimethylcelecoxib, or a celecoxib analog.

4. The combination pharmaceutical of claim 1, wherein the $\beta$-adrenergic receptor agonist is formoterol.

5. A method of treating a bronchospastic condition that can lead to airway obstruction in a living body, the method comprising administering the combination pharmaceutical of claim 1 to the living body in a therapeutic amount sufficient to activate the Kv7 potassium channels of an airway smooth muscle cell.

6. The method of claim 5, wherein the bronchospastic condition is an asthmatic condition.

7. The method of claim 5, wherein the airway smooth muscle cell is in a wall of a bronchiole of a lung.

8. The method of claim 5, wherein the pharmaceutical is administered to the living body as an inhalant.

9. A method of treating a bronchospastic condition that can lead to airway obstruction in a living body, the method comprising:
   administering a pharmaceutical to a lipid membrane of a mammalian cell;
   measuring an electrical activity across the lipid membrane to determine if the pharmaceutical activates Kv7 potassium channels of the lipid membrane of an airway smooth muscle cell; and then
   administering the pharmaceutical and a second pharmaceutical to the living body in a therapeutic amount sufficient to activate the Kv7 potassium channels of an airway smooth muscle cell, wherein the second pharmaceutical comprises a $\beta$-adrenergic receptor agonist, sustained or repetitive exposure by a subject to the $\beta$-adrenergic receptor agonist induces receptor desensitization in the subject, and the combination of the $\beta$-adrenergic receptor agonist and the pharmaceutical mitigates the effects of the receptor desensitization induced by the $\beta$-adrenergic receptor agonist.

10. The method of claim 9, wherein the pharmaceutical is administered to the living body as an inhalant.

11. The method of claim 9, wherein the bronchospastic condition is an asthmatic condition.

12. The method of claim 9, wherein the pharmaceutical comprises a compound chosen from the group consisting of retigabine, zinc pyrithione, flupirtine, celecoxib, dimethylcelecoxib, or a celecoxib analog.

13. The method of claim 9, wherein the airway smooth muscle cell is in a wall of a bronchiole of a lung.

14. The method of claim 9, wherein the β-adrenergic receptor agonist is formoterol.

15. A method of treating a bronchospastic condition that can lead to airway obstruction in a living body, the method comprising:

administering a pharmaceutical and a second pharmaceutical to the living body in a therapeutic amount sufficient to activate the Kv7 potassium channels of an airway smooth muscle cell, wherein the pharmaceutical comprises a compound chosen from the group consisting of zinc pyrithione, flupirtine, celecoxib, dimethylcelecoxib, or a celecoxib analog, the second pharmaceutical comprises a β-adrenergic receptor agonist to the living body, sustained or repetitive exposure by a subject to the β-adrenergic receptor agonist induces receptor desensitization in the subject, and the combination of the β-adrenergic receptor agonist and the pharmaceutical mitigates the effects of the receptor desensitization induced by the β-adrenergic receptor agonist.

* * * * *